(12) United States Patent
Domel et al.

(10) Patent No.: US 8,968,179 B2
(45) Date of Patent: Mar. 3, 2015

(54) PATIENT-MANIPULABLE DEVICE FOR AMELIORATING INCONTINENCE

(75) Inventors: Douglas R. Domel, Santa Clarita, CA (US); Robert Reese Neyland, Santa Clarita, CA (US); Tabitha S. McNaught, Sterling, VA (US)

(73) Assignee: Innovision Devices, LLC, Santa Clarita, CA (US)

( * ) Notice: Subject to any disclaimer, the term of this patent is extended or adjusted under 35 U.S.C. 154(b) by 224 days.

(21) Appl. No.: 13/567,017

(22) Filed: Aug. 4, 2012

(65) Prior Publication Data

US 2014/0039242 A1 Feb. 6, 2014

(51) Int. Cl.
*A61F 2/04* (2013.01)
*A61F 2/00* (2006.01)

(52) U.S. Cl.
CPC ............... *A61F 2/0036* (2013.01); *A61F 2/004* (2013.01)
USPC .......................................... 600/30

(58) Field of Classification Search
CPC ..................... A61B 2017/00805; A61F 2/004; A61F 2/0036; A61F 2210/009
USPC ............................... 600/29, 30, 37
See application file for complete search history.

(56) References Cited

U.S. PATENT DOCUMENTS

| 3,815,576 | A | * | 6/1974 | Balaban ........................ 600/30 |
| 4,453,536 | A | * | 6/1984 | Abild ............................. 600/30 |
| 4,553,533 | A | | 11/1985 | Leighton |
| 4,632,114 | A | | 12/1986 | Todd et al. |
| 5,366,506 | A | | 11/1994 | Davis |
| 6,090,098 | A | | 7/2000 | Zunker et al. |
| 6,409,656 | B1 | * | 6/2002 | Sangouard et al. ............ 600/30 |
| 2012/0010462 | A1 | | 1/2012 | MacLean |
| 2012/0130157 | A1 | | 5/2012 | Cotner et al. |

OTHER PUBLICATIONS

Shahar Madjar, Shilomo Raz, Angelo E. Gousse, "Fixed and Dynamic Urethral Compression for the Treatment of Post-Prostatectomy Urinary Incontinence: Is History Repeating Itself?" The Journal of Urology, vol. 166, 411-415, Aug. 2001.

Virgilio G. Petero, Jr. and Ananias C. Diokno, "Comparison of the Long-Term Outcomes Between Incontinent Men and Women Treated with Artificial Urinary Sphincter". The Journal of Urology, vol. 175, 605-609, Feb. 2006.

UROVALVE website print out Company Fact Sheet. Printed Jul. 2012.

* cited by examiner

*Primary Examiner* — Christine H Matthews
*Assistant Examiner* — Joshua D Lannu
(74) *Attorney, Agent, or Firm* — John L. Rogitz

(57) ABSTRACT

An implantable device arranged to contact the urethral sphincter allows for manipulation of the device from outside the body by the patient.

14 Claims, 6 Drawing Sheets

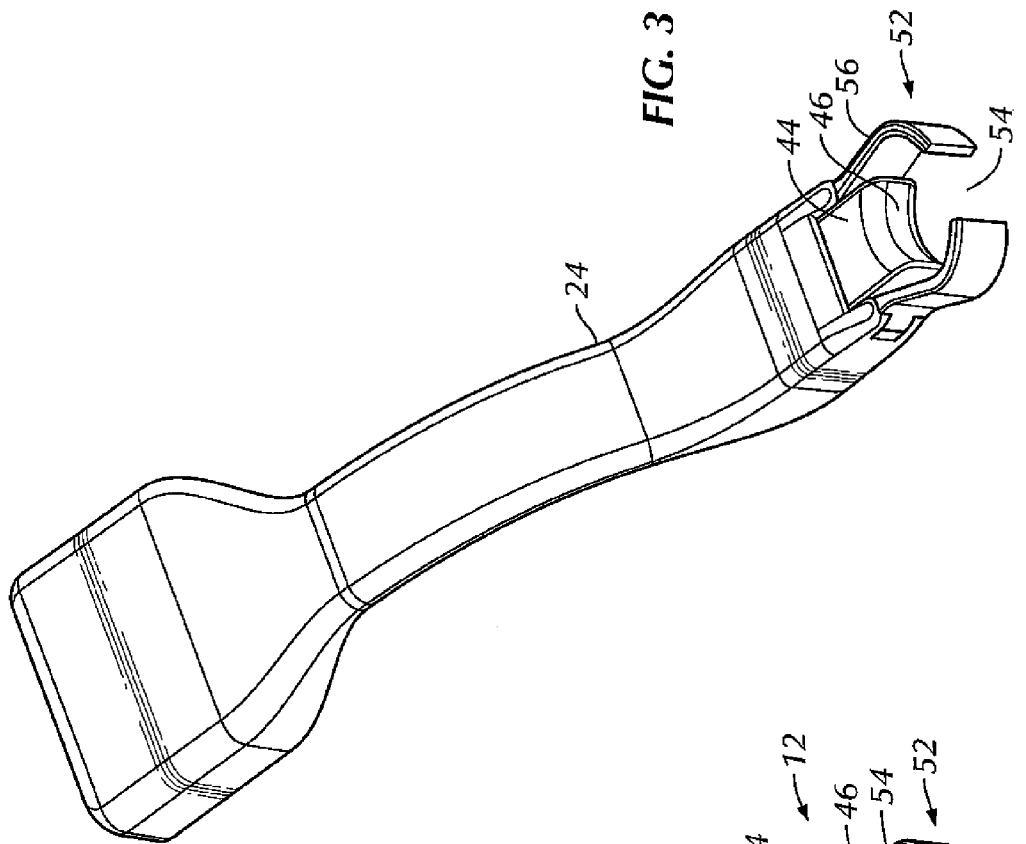
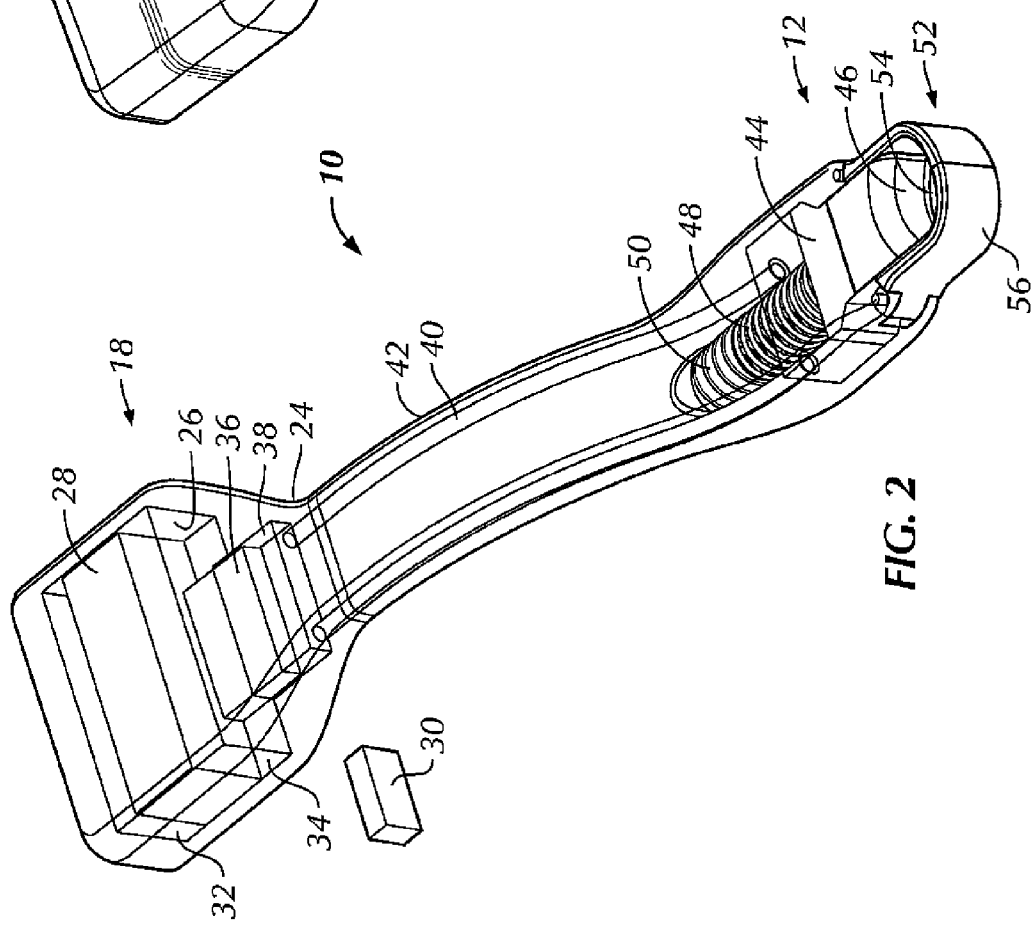

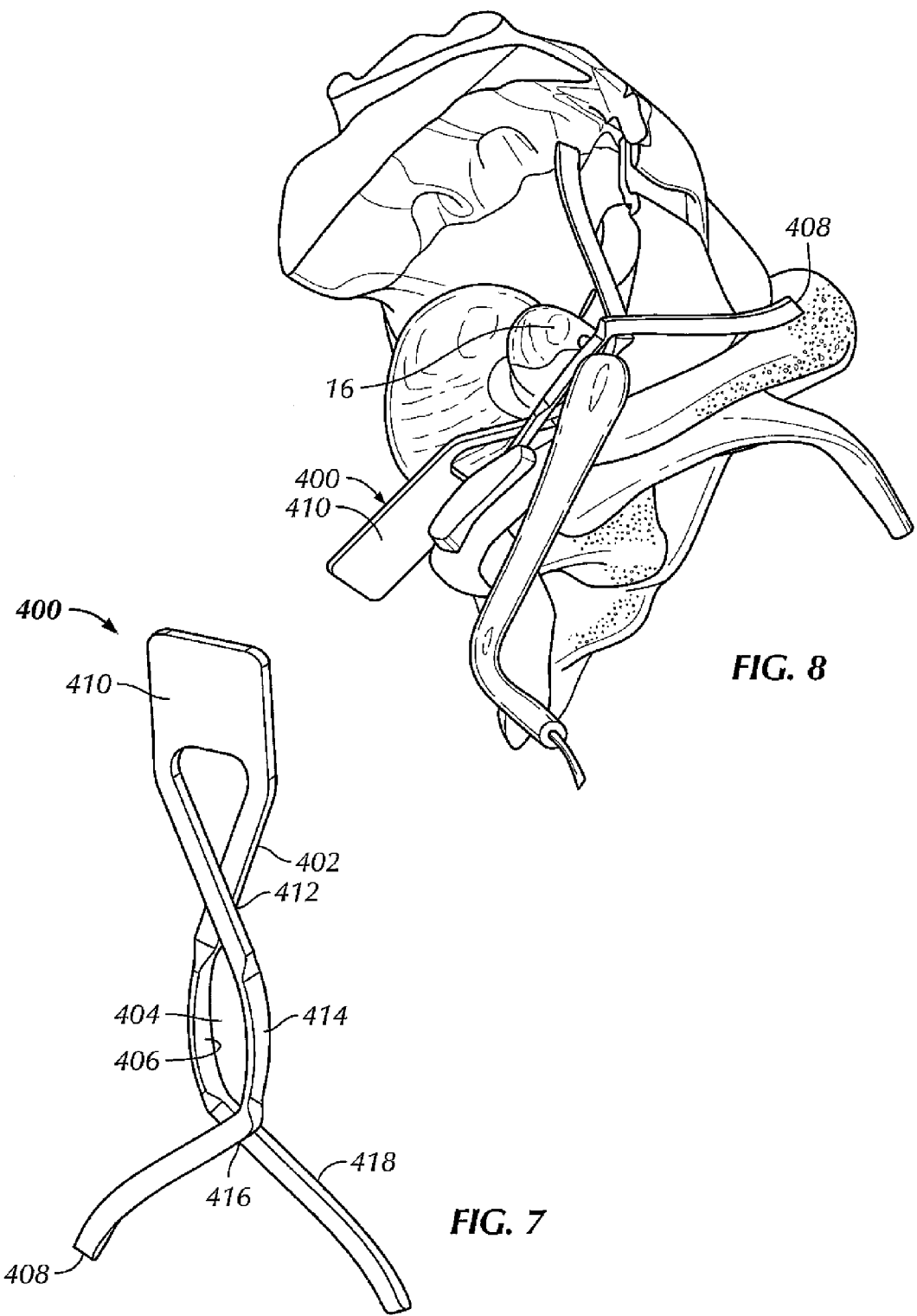

PATIENT-MANIPULABLE DEVICE FOR AMELIORATING INCONTINENCE

FIELD OF THE INVENTION

The present application relates generally to patient-manipulable devices for ameliorating incontinence.

BACKGROUND OF THE INVENTION

Urinary incontinence can have a variety of causes. Such incontinence results when the urethral sphincter does not close sufficiently to block urine flow through the urethra. A second urinary sphincter malady is urinary retention, which can be caused by spinal cord injury. Urinary retention is the outcome of the urethral sphincter not voluntarily relaxing and opening to allow the urethra to open, causing a state of permanent urinary retention. Particularly in the case of males, there is not much real estate with which to work on the urethra since the prostate surrounds a portion of the urethra, dividing the sphincter muscle into two, whereas for females the sphincter extends along the urethra from the bladder to near where it opens to the outside of the body.

A common treatment for incontinence is simply inserting a catheter into the urethra. Not only is this an uncomfortable nuisance for the patient, it entails the risk that of urinary tract infections (UTI), which increase in frequency with the number of catheterizations required.

Another treatment which is useful for males only is the use of a so-called artificial urinary sphincter/urethral cuff, in which a working fluid can inflate a cuff that is implanted around the urethra. The working fluid is infused and removed from the cuff pumped by squeezing a pump surgically located in the scrotum. Not only can this device not be used in females, it entails the risk of injury to the scrotum, and patients find it a nuisance to feel for the pump in the scrotum. Moreover, fine tuning the relatively cumbersome cuff to the patient is not possible.

For females, pubovaginal slings made of tissue have been provided in which titanium screws are placed in the pelvic bone on both the sides of the urethra. These screws are attached to sutures that support a strip of tissue that is passed beneath the urethra to support the urethra and the bladder, so that the leakage does not occur during coughing, sneezing, laughing or other physical activities. This procedure does not allow for patient control, and entails a risk of perforation of the urethra or bladder neck due to elevated pressure. A similar approach with similar problems is the use of tension-free vaginal tape in which a "hammock" is wrapped around a portion of the abdominal muscle instead of held in place by screws. There is a risk of perforation of the urethra or bladder neck due to elevated pressure, and the device does not compensate for change due to movement of the abdominal muscles due to weight loss or gain, which could lead to stresses that could cause serious damage. Or, ligaments can be attached to a sagging bladder neck and urethra that have dropped abnormally low in the pelvic area, but as understood herein, this procedure caries many of the risks noted above, and also the risk of tearing/bleeding at the sutures attached to the vaginal wall.

SUMMARY OF THE INVENTION

Accordingly, a device includes a pressure element formed with a pressure surface juxtaposable with the urethral sphincter of a patient. An actuator extends away from the pressure element and is engaged therewith. The actuator can be manipulable by the patient from outside the body of the patient to move the pressure element between a retracted position, in which the pressure surface exerts no more than a first pressure on the urethral sphincter, and an advanced position, in which the pressure surface exerts at least a second pressure on the urethral sphincter. The second pressure is greater than the first pressure, such that in the advanced position incontinence is ameliorated.

In an example embodiment, the actuator includes a magnet and a coupler coupling the magnet to the pressure element. In this embodiment, the magnet is movable within the patient by a patient-held actuator magnet moved by the patient outside the patient's body. The pressure surface is established by a distal end of the pressure element for contacting the urethral sphincter, and if desired the pressure surface can be a continuous curved surface. If desired, a spring may be coupled to the pressure element to bias the pressure element toward the advanced position, and an adjustment mechanism can be coupled to the spring to establish a compression of the spring.

As set forth further below, a distal urethra closure establishes, along with the pressure surface, an enclosure in which the urethra can be received. The distal urethra closure may be detachable from the device to permit a surgeon to position the pressure surface next to the urethral sphincter. The distal urethra closure can then be engaged with the device to hold the urethra within the enclosure. Or, the distal urethra closure may hinge on the device between an open configuration, in which the urethra may pass into the enclosure, and a closed configuration, in which the urethra may not pass into the enclosure.

In alternate examples, the pressure surface is established by opposed arms each defining a distal end with at least one arm being hinged on the device. The distal ends are distanced from each other in an open configuration to permit the urethra to pass between the arms. Also, the distal ends can be juxtaposed with other in a closed configuration to prevent the urethra from passing between the arms. In this embodiment, the arms can terminate at the respective distal ends. On the other hand, in a sub-embodiment each arm loops back on itself at the respective distal end such that each arm forms a slot into which a portion of the urethral sphincter can be received, such that the urethral sphincter is urged to open the urethra in the open configuration to alleviate urinary retention and such that the urethral sphincter is urged to close in the closed configuration to alleviate incontinence.

In yet another non-limiting example the pressure element includes first and second curved arms that criss-cross each other to form a bight into which the urethral sphincter can be positioned. The pressure surface is defined by portions of inner surfaces of the arms bordering the bight. Distal ends of the pressure actuator are engageable with bone structure in the patient. In this embodiment, the actuator includes a manipulator tab positionable under the skin of the patient to permit the patient to urge the arms against the bone structure, thereby enlarging the bight. The manipulator tab is releasable by the patient to permit the arms under material bias to move to shrink the bight around the urethra.

In another aspect, a method includes implanting a device in the retropubic space of a patient, with a manipulator member of the device juxtaposed with the top of the pubic symphysis and with the device extending between the pubis and the bladder toward the urethra. The method includes engaging a pressure element of the device with the urethral sphincter. The device has a configuration in which the device applies pressure to the urethral sphincter to alleviate incontinence.

In another aspect, an assembly includes an implantable device configured to contact the urethral sphincter. The device includes a reciprocatingly arranged slidable pressure element to selective apply pressure to the urethral sphincter responsive to manipulation from outside the body to alleviate incontinence, with no portions of the device extending outside the body.

In another aspect, an implantable device is configured to contact the urethral sphincter. The device includes a C-shaped inflatable cuff defining a longitudinally open slit and central channel. The cuff has a deflated configuration, in which the slit is large enough to accept the urethra of a patient therethrough into the central channel, and an inflated configuration in which the slit is not large enough to allow the urethra to pass therethrough and the cuff exerts surrounding pressure on the urethral sphincter to ameliorate the effects of incontinence. A movable actuator selectively urges the cuff toward the inflated configuration.

The details of the present invention, both as to its structure and operation, can best be understood in reference to the accompanying drawings, in which like reference numerals refer to like parts, and in which:

BRIEF DESCRIPTION OF THE DRAWINGS

FIG. 2 is a perspective view of a first embodiment with the outer surface transparent to illustrate interior components, with the distal urethra closure in the closed configuration and the pressure element midway between the advanced position and retracted position;

FIG. 3 is a perspective view of the first embodiment with the distal urethra closure in the open configuration and the pressure element in the retracted position;

FIG. 7 is a perspective view of a fifth embodiment in which the pressure element includes first and second curved arms that criss-cross each other to form a bight into which the urethral sphincter can be positioned;

FIG. 8 is a perspective view of the fifth embodiment showing the distal ends of the pressure actuator engaged with the pelvis of the patient such that when the patient presses the manipulator tab, which is positioned under the skin of the patient, the arms are urged against the pelvis, thereby enlarging the bight, with the manipulator tab being releasable by the patient to permit the arms under material bias to move to shrink the bight around the urethra;

DETAILED DESCRIPTION OF THE PREFERRED EMBODIMENT

Figure 1:
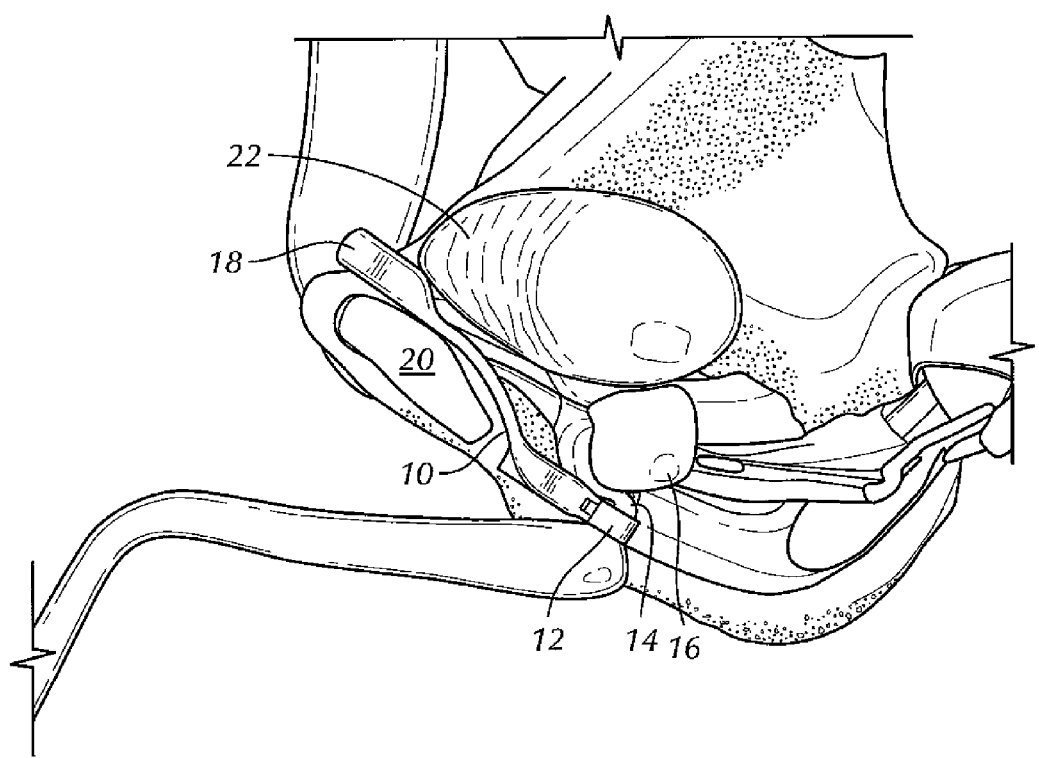
FIG. 1 is a perspective view showing a first embodiment of the device engaged with a male's urethral just below the prostate gland.

Referring initially to FIG. 1, a device 10 includes a fluidless pressure element assembly 12 engaged with the urethral sphincter 14 of a patient, just below the prostate gland 16. An actuator 18 of the device 10 extends away from the pressure element assembly 12 to form an elongated, relatively thin device 10, and as described further below, the actuator 18 can be manipulated by the patient from outside the body of the patient to move the pressure element assembly 12 between a retracted position, in which a pressure surface of the pressure element assembly 12 exerts no more than a first pressure on the urethral sphincter and preferably exerts no pressure at all on the sphincter, and an advanced position, in which the pressure surface exerts pressure on the urethral sphincter such that in the advanced position incontinence is ameliorated.

In the example shown, when implanted the device 10 occupies the retropubic space, extending from the top of the pubic symphysis through the space between the pubis 20 and the bladder 22, down towards the urethra. Present principles recognize that the retropubic space has certain advantages. It is relatively 'open', being occupied by only soft tissue. Also, the pelvis protects the device 10 from accidental damage due to force exerted on the outside of the body near to it. The retropubic space can be accessed surgically either from above (over top of pubis) or below (up through the perineum).

In an embodiment described below, in which the actuator 18 includes a magnet, the magnet resides in the end above the pubic symphysis, near the abdominal wall, and is located such that if a magnet with sufficiently large 'pull' is held up to the abdomen outside the body in the vicinity of the device magnet, sufficient force is exerted by the exterior magnet to attract the device magnet and actuate the device. If desired, the actuator end of the device with the internal magnet may be fixed to the back of the pubis (e.g., by suturing) to prevent damage to the urethra due to undesired movement of the device body caused by movement or pull of internal magnet.

A minimally invasive implantation procedure can be employed when placing and tuning the device 10. The slim profile of the device would allow the device to pass through a relatively small opening. The exterior housing of the device 10 can be made of a biocompatible material such as but not limited to Salubria.

FIG. 2 shows details of an example embodiment of the device 10. As shown, the actuator 18 includes a biocompatible housing 24 with a magnet enclosure 26 configured to closely receive a permanent magnet 28 therein. The magnet 28 can slide within the enclosure 26 under the influence of a magnetic force from a patient-holdable actuator magnet 30 located outside the body.

In the example shown, the permanent magnet 28 is parallelepiped-shaped as is the enclosure 26, and the magnet 28 can slide from a rear wall 32 of the enclosure 26 to a front wall 34. The width and depth of the enclosure 26 may be slightly larger than the width and depth of the magnet 28. If desired, a magnetic or non-magnetic extension 36 can be provided on a front face of the magnet 28 and can slide in an extension enclosure 38 that is contiguous to the enclosure 26 which holds the permanent magnet 28. As was the case with the magnet 28/enclosure 26, the extension enclosure 38 is but marginally larger in width and thickness than the extension 36, so that the enclosures 26, 38 closely bear the respective magnet 28/extension 36 as the magnet 28 and extension 36 slide together along the longitudinal axis of the device 10 between the retracted and extended positions under the influence of the actuator magnet 30.

A coupler couples the magnet 28 to the pressure element assembly 12. In the embodiment shown, the coupler is established by two elongated axially stiff wires, lines, or rods 40 that extend through an elongated connector segment 42 of the housing 26 from the extension 36 to a slidable pressure element 44 of the pressure element assembly 12. A distal end 46 (which may be a continuous curved surface such as concave as shown) of the pressure element 44 establishes a pressure surface that faces the urethral sphincter surrounding the urethra when the device 10 is implanted as shown in FIG. 1.

In the example shown, a leaf or more preferably coil spring 48 is disposed in the housing 24 in compressive contact with the pressure element 44 to bias the pressure element 44 toward an advanced position, in which the pressure element 44 exerts a pressure on the urethral sphincter which is greater than the pressure exerted by the pressure element 44 on the sphincter when the pressure element 44 is in a retracted position away from the sphincter. Note that in the retracted position, the pressure element 44 may exert little or no pressure on the sphincter and urethra. In any case, it may now be readily appreciated that when a person moves the actuator magnet 30 outside the body and relatively closely spaced from the permanent magnet 28 (typically separated only by a few centimeters of soft tissue), the magnetic coupling between the magnets enables a person to move the permanent magnet and, hence, the pressure element 44 between the advanced and retracted positions to respectively close off the urethra to ameliorate incontinence, and to permit the urethra to open to pass urine.

If desired, an adjustment mechanism 50 may be coupled to the spring 48 to establish a compression of the spring and hence a preloading of the compressive force exerted by the pressure element 44 on the urethra, to "fine tune" the operation of the device to the particular physiology of the patient. In the example shown, the adjustment mechanism 50 is a set screw threadably engaged with the housing 24 in contact with the spring 48. A surgeon may advance or retract the set screw by rotating it as appropriate to establish a clinically appropriate compression preload on the pressure element 44.

In non-limiting examples, a catheter-borne pressure sensor can be used to measure pressure within the urethra while a tool such as an Allen wrench is used to adjust the screw depth until the desired pressure was attained. This ensures that the device did not exert over-pressure, which could cause damage to the sphincter and/or urethra, or under-pressure, defined as pressure too low to reliably maintain continence. In embodiments in which permanent retention is an issue, the spring 48 may be dispensed with.

In cross-reference to FIGS. 2 and 3, a distal urethra closure establishes, along with the pressure surface 46 of the pressure element 44, an enclosure 54 in which the urethra can be received. In one example, the distal urethra closure includes first and second curved closure arms 56 that are hingedly engaged with the housing 24 between an open configuration (FIG. 3), in which the urethra may pass into the enclosure 54, and a closed configuration (FIG. 2), in which the urethra may not pass into (or out of) the enclosure 54. The surgeon manually moves the arms 56 to the open configuration, advances the device 10 to the urethra until the urethra is positioned in the enclosure 54, and then closes the arms. The arms may be held closed by a friction fit between the arms and the housing, solvent bonding applied by the surgeon, sutures, a clip structure on one arm engaging a recess in the other arm, or other suitable closure methods.

Figure 4:
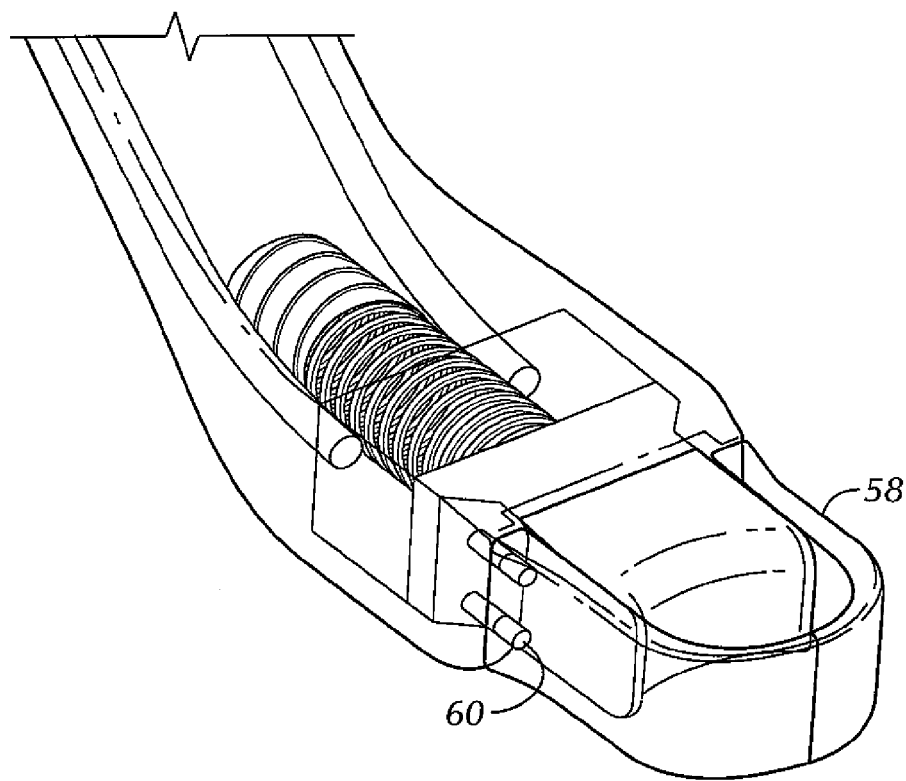
FIG. 4 is a perspective view of the distal part of a second embodiment with the outer surface transparent to illustrate interior components, showing a distal urethra closure that is detachable from the device to permit a surgeon to position the pressure surface next to the urethral sphincter, with the distal urethra closure then being engageable with the device as shown to hold the urethra within the enclosure.

Alternatively, FIG. 4 illustrates a unitary closure element 58 that is detachable from the device to permit a surgeon to position the pressure surface next to the urethral sphincter, with the distal urethra closure then being engageable with the device to hold the urethra within the enclosure. In the embodiment shown, channels in the closure element 58 can be engaged with complementarily-shaped and -sized pins 60 in the housing, with two pins on each side as shown in the example embodiment of FIG. 4. A friction fit between the closure element 58 and pins 60 (or other appropriate fixation structure) can be used to hold the closure element 58 onto the housing of the device as shown in FIG. 4.

Figure 5:
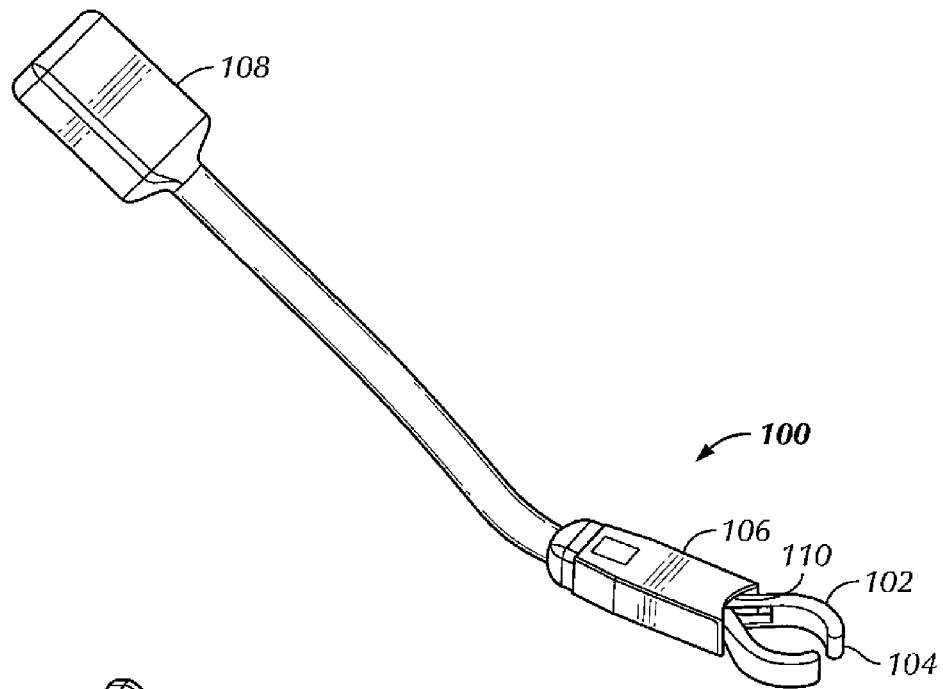
FIG. 5 is a perspective view of a third embodiment showing a pressure element established by opposed curved arms.
Figure 6:
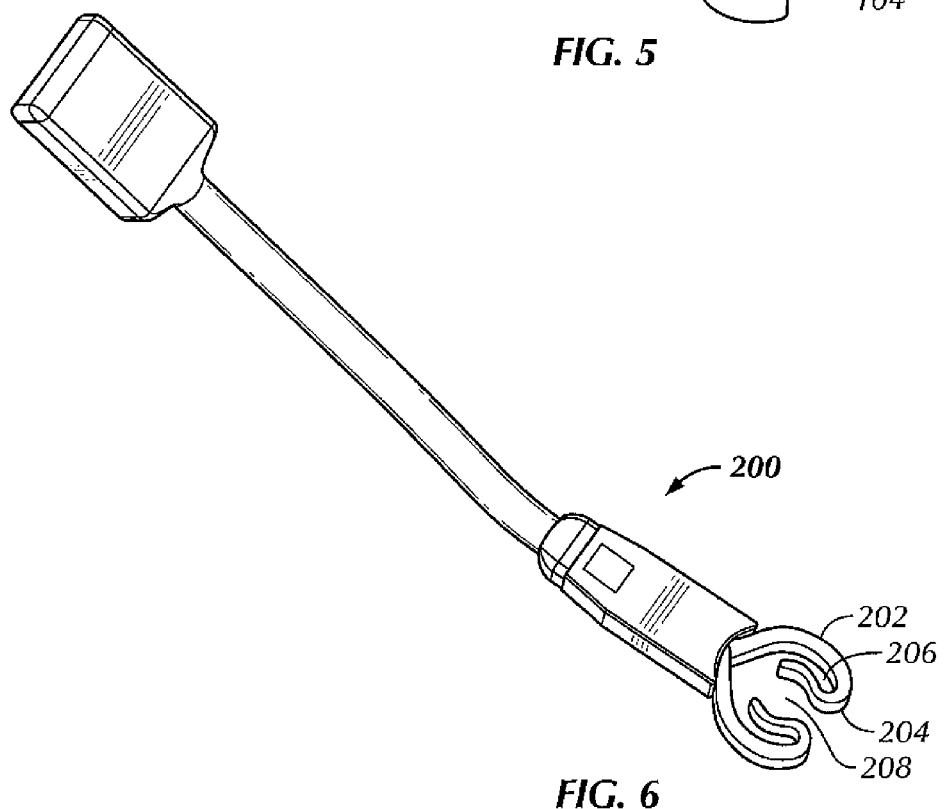
FIG. 6 is a perspective view of a fourth embodiment showing a pressure element established by opposed curved arms each of which loops back on itself at the respective distal end such that each arm forms a slot into which a portion of the urethral sphincter can be received, such that the urethral sphincter is urged to open the urethra in the open configuration to alleviate urinary retention and such that the urethral sphincter is urged to close in the closed configuration to alleviate incontinence.
Figure 9:
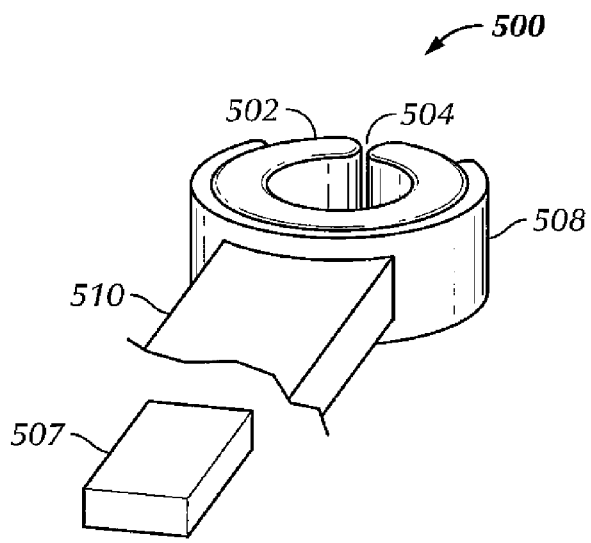
FIG. 9 is a perspective of a sixth embodiment of a pressure element established by an inflatable cuff.
Figure 10:
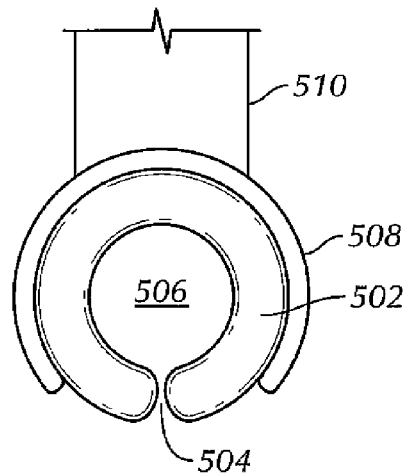
FIG. 10 is a front elevational view of the embodiment shown in FIG. 9 in the inflated configuration.
Figure 11:
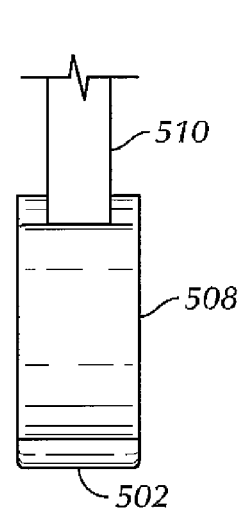
FIG. 11 is a side elevational view of the embodiment shown in FIG. 9.
Figure 12:
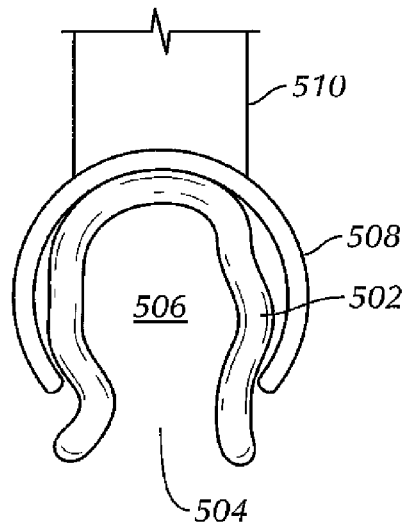
FIG. 12 is a front elevational view of the embodiment shown in FIG. 9 in the deflated configuration.

Refer now to FIGS. 5 and 6, which show respective alternate embodiments that in all essential respects are identical to that shown in FIGS. 2 and 3 with the following exceptions. In FIG. 5, a pressure element of a device 100 is established by opposed curved arms 102 each defining a respective distal end 104, with at least one arm and preferably both arms 102 being hinged on a housing 106 of the device 100. When the permanent magnet in a magnet housing 108 of the device 100 is retracted (away from the urethra), the arms 102 are retracted into a distal opening 110 of the housing 106 with the outer surfaces of the arms 102 riding against the periphery of the opening 110, which urges the arms 102 to pivot so that the distal ends 104 move toward each other to establish a closed configuration to trap the urethra between the arms. On the other hand, when the magnet is moved toward the urethra the arms 102 move outward, pivoting under, e.g., the influence of material bias as they clear the opening 110 to an open configuration in which the distal ends 104 are distanced from each other to establish an open configuration to permit the urethra to pass between the arms. In FIG. 5, the arms 102 terminate at the respective distal ends 104.

In contrast, FIG. 6 shows a device 200 which is substantially identical to the device 100 shown in FIG. 5 except that each of two arms 202 loops back on itself at a respective distal end 204 such that each arm 202 forms a respective slot 206. A portion of the urethral sphincter can be received in the slots 206 with the urethra itself remaining in a central enclosure 108. This is possible because the urethral sphincter is horseshoe-shaped and does not completely surround the urethra. With the device 200, the urethral sphincter can be urged to open the urethra by moving the permanent magnet toward the urethra to cause the arms 202 to pivot open, pulling the sphincter outwardly from the urethra. This alleviates urinary retention. Also, the urethral sphincter is urged to close when the arms are pulled away from the urethra to alleviate incontinence.

FIGS. 7 and 8 illustrate yet another alternate incontinence relief device 400 that can be engaged with the urethral sphincter to close it off. In the device 400, which may be made of a single unitary piece of biocompatible plastic, a pressure element is established by first and second curved flexible arms 402 that criss-cross each other to form a bight 404 into which the urethral sphincter can be positioned. A pressure surface is defined by portions 406 of inner surfaces of the arms bordering the bight.

Distal free ends 408 of the arms 402 can be engaged with bone structure in the patient such as the pelvis. Opposite the free ends 408, a solid, preferably rectilinear manipulator tab 410 is coupled to the arms 402 and may be positioned under the skin of the patient to permit the patient to urge the arms 402 against the bone structure, thereby enlarging the bight 408. The manipulator tab can then be released by the patient to permit the arms 402 under material bias to move to shrink the bight 408 around the urethra to alleviate incontinence.

In the specific example shown, the arms 402 are coupled to opposed outer edges of the tab 410. The arms 402 extend inwardly from the tab, crossing each other at 412, then curve in respective convex segments 414 to establish the bight 404, crossing each other again at 416 and continuing to extend away from each other along distal segments 418 to the distal ends 408. Because they are flexible, a surgeon can pull the distal segments 418 of the arms 402 away from each other sufficiently to pass the urethra between the arms into the bight 404, at which point the arms are released to move back toward each other, closing the bight and trapping the urethra therein. The tab 410 is surgically located above the pubic symphysis, similar to the previous embodiments, such that pressure with a finger or palm on the lower abdomen exerts pressure on the tab 410. The resulting mechanical deflection causes the arms 402 bow outwards, relaxing the pressure on the urethra and allowing for normal voiding.

It may now be appreciated that the devices herein require no mechanical or electrical connections outside the patient while avoiding infections that can be caused by catheters. Not only do the devices assist in alleviating incontinence, but they also do not destroy anything in the body. Beneficially, implantation may be done clinically without the need for the patient to spend the night at a hospital, and the chance for infection is much lower because nothing crosses the boundary between the inside and outside of the body since there is no way for infection to get in. The implanted device has an adjustability quality because it assists the sphincter as set when implanted, so it will provide the appropriate pressure required to prevent incontinence.

FIGS. 9-12 show an alternate device 500 that is established by a C-shaped inflatable cuff 502 defining a longitudinally open slit 504 and central channel 506. The cuff 502 has a deflated configuration (FIG. 12), in which the slit 504 is large enough to accept the urethra of a patient therethrough into the central channel 506. Also, the cuff 502 has an inflated configuration (FIGS. 9 and 10) in which the slit 504 is not large enough to allow the urethra to pass therethrough and the cuff 502 exerts an even, surrounding pressure on the urethral sphincter to ameliorate the effects of incontinence. A reciprocatingly arranged actuator 507 such as a magnet can be moved to selectively urge the cuff 502 toward the inflated configuration. As was the case with the previous embodiments, the actuator is manipulable by the patient from outside the body of the patient to move the cuff 502.

As shown, a rigid plastic or metal C-shaped support 508 surrounds the cuff 502 in contact with the cuff such that inflation of the cuff does not change the outer diameter of the cuff, being constrained by the support 508, but only causes the inner diameter of the cuff to decrease. A cylindrical or rectilinear inflatable tube 510 may be in fluid communication with the cuff 502, extending away from the cuff through an opening in the support 508 as shown. The actuator 507 bears against the tube 510 to urge fluid in the tube into the cuff and thereby urge the cuff toward the inflated configuration.

In operation, the surgeon advances the cuff in the deflated configuration around the urethral sphincter through the slot 504. The cuff 502 and tube 510 are then inflated with a working fluid such as a flowable silicone used in breast implants or saline. The amount of inflation is as clinically necessary to close the urethra of the particular patient. Subsequent movement of the actuator 507 (e.g., by moving a magnet outside the body to move a magnetic-based actuator 507) against the tube 510 squeezes the tube, urging fluid from the tube into the cuff 502 to cause it to clamp down on the urethral sphincter. In alternate structural cooperation the actuator 507 may be moved to relieve pressure on the tube and, hence, on the cuff to facilitate voiding by the patient.

While the particular PATIENT-MANIPULABLE DEVICE FOR AMELIORATING INCONTINENCE is herein shown and described in detail, it is to be understood that the subject matter which is encompassed by the present invention is limited only by the claims.

What is claimed is:

1. A device comprising:
   a fluidless pressure element formed with a pressure surface juxtaposable with the urethral sphincter of a patient's body, wherein the pressure surface is comprised of opposed arms each defining a distal end and at least one of the opposed arms is hingedly movable, the distal ends being distanced from each other in an open configuration to permit the urethra to pass between the arms, the distal ends being juxtaposed with each other in a closed configuration to prevent the urethra from passing between the arms; and
   an actuator extending away from the pressure element and engaged therewith, the actuator being manipulable by the patient from outside the body of the patient to move the pressure element between a retracted position, in which the pressure surface exerts no more than a first pressure on the urethral sphincter, and an advanced position, in which the pressure surface exerts at least a second pressure on the urethral sphincter, the second pressure being greater than the first pressure, such that in the advanced position incontinence is ameliorated.

2. The device of claim 1, wherein the actuator includes a magnet and a coupler coupling the magnet to the pressure element, the magnet being movable within the patient by a patient-held actuator magnet moved by the patient outside the patient's body.

3. The device of claim 1, wherein the pressure surface is comprised at least in part by the distal ends of the pressure element.

4. The device of claim 3, wherein the pressure surface is a continuous curved surface.

5. The device of claim 1, comprising a spring coupled to the pressure element to bias the pressure element toward the advanced position.

6. The device of claim 5, comprising an adjustment mechanism coupled to the spring to establish a compression of the spring.

7. The device of claim 3, comprising a distal urethra closure to establish, along with the pressure surface, an enclosure in which the urethra can be received.

8. The device of claim 7, wherein the distal urethra closure is detachable from the device to permit a surgeon to position the pressure surface next to the urethral sphincter, the distal urethra closure then being engageable with the device to hold the urethra within the enclosure.

9. The device of claim 1, wherein the arms terminate at the respective distal ends.

10. The device of claim 1, wherein each arm loops back on itself at the respective distal end such that each arm forms a slot into which a portion of the urethral sphincter can be received, such that the urethral sphincter is urged to open the urethra in the open configuration to alleviate urinary retention and such that the urethral sphincter is urged to close in the closed configuration to alleviate incontinence.

11. An assembly comprising:
    an implantable device configured to contact the urethral sphincter of a patient's body, the device including a pressure element to selectively apply pressure to the urethral sphincter responsive to manipulation from outside the patient's body having the urethral sphincter to alleviate incontinence, wherein a pressure surface is comprised of opposed arms of the pressure element and each defining a distal end and at least one of the opposed arms being hingedly movable on the device, the distal end being distanced from each other in an open configuration to permit the urethra to pass between the arms, the distal ends being juxtaposed with each other in a closed configuration to prevent the urethra from passing between the opposed arms, wherein the pressure element is formed with a pressure surface juxtaposable with the urethral sphincter of the patient, and the device includes an actuator extending away from the pressure element and engaged therewith, the actuator being manipulable by the patient from outside the body of the patient to move the pressure element between a retracted position, in which the pressure surface exerts no more than a first pressure on the urethral sphincter, and an advanced position, in which the pressure surface exerts at least a second pressure on the urethral sphincter, the second pressure being greater than the first pressure, such that in the advanced position incontinence is ameliorated.

12. The assembly of claim 5, wherein the actuator includes a magnet and a coupler coupling the magnet to the pressure element, the magnet being movable within the patient by a patient-held actuator magnet moved by the patient outside the patient's body.

13. The assembly of claim 12, comprising a distal urethra closure to establish, along with the pressure surface, an enclosure in which the urethra can be received.

14. An assembly comprising:
an implantable device configured to contact the urethral sphincter of a patient's body, the device including a pressure element to selectively apply pressure to the urethral sphincter responsive to manipulation from outside the body of the patient having the urethral sphincter to alleviate incontinence, wherein a pressure surface is comprised of opposed arms of the pressure element and each defining a distal end and at least one of the opposed arms being hingedly movable on the device, the distal end being distanced from each other in an open configuration to permit the urethra to pass between the arms, the distal ends being juxtaposed with each other in a closed configuration to prevent the urethra from passing between the opposed arms, wherein each arm loops back on itself at the respective distal end such that each arm forms a slot into which a portion of the urethral sphincter can be received, such that the urethral sphincter is urged to open the urethra in the open configuration to alleviate urinary retention and such that the urethral sphincter is urged to close in the closed configuration to alleviate incontinence.

* * * * *